United States Patent [19]

Arkles

[11] Patent Number: 5,371,262
[45] Date of Patent: Dec. 6, 1994

[54] HYDROXYMETHYLTRIALKOXYSILANES AND METHODS OF MAKING AND USING THE SAME

[75] Inventor: Barry C. Arkles, Dresher, Pa.

[73] Assignee: Gelest, Inc., Tullytown, Pa.

[21] Appl. No.: 29,217

[22] Filed: Mar. 10, 1993

[51] Int. Cl.$^5$ ............................................. C07F 7/08
[52] U.S. Cl. ................................. 556/449; 556/440; 556/443
[58] Field of Search .................. 556/443, 449, 440

[56] References Cited

U.S. PATENT DOCUMENTS

| | | | |
|---|---|---|---|
| 2,527,590 | 10/1950 | Speier | 556/449 |
| 2,527,591 | 10/1950 | Speier | 556/449 |
| 2,582,569 | 1/1952 | Speier | 556/449 |
| 2,629,727 | 2/1953 | Speier | 556/449 |
| 2,924,588 | 2/1960 | Speier | 556/449 X |
| 3,159,496 | 12/1964 | Rossmy et al. | 556/449 X |
| 3,317,460 | 5/1967 | Clark et al. | 556/449 X |
| 3,355,473 | 11/1967 | Clark et al. | 556/449 |
| 3,442,925 | 5/1969 | Simmler et al. | 556/449 |
| 3,622,609 | 11/1971 | Mironov et al. | 556/449 |
| 5,159,095 | 10/1992 | Celebuski | 556/449 X |

OTHER PUBLICATIONS

Ph. Colomban, "Gel Technology in Ceramics, Glass-Ceramics and Ceramic-Ceramic Composites," *Ceramics International*, 1989, pp. 23–50.

Primary Examiner—Paul F. Shaver
Attorney, Agent, or Firm—Panitch Schwarze Jacobs & Nadel

[57] ABSTRACT

Novel hydroxymethyltrialkoxysilanes of the formula:

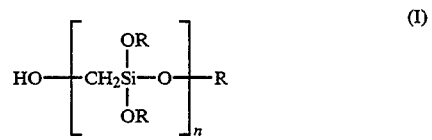

are produced by transesterifying a carboxylic acid ester of hydroxymethyltrialkoxysilane with an alcohol, and distilling the reaction mixture to remove the carboxylate of the alcohol. The carboxylic acid ester of hydroxymethyltrialkoxysilane is prepared by the reaction of an alkali metal carboxylate with chloromethyltrialkoxysilane, which in turn is prepared by the reaction of a trialkylorthoester with chloromethyltrichlorosilane by heating to reflux with removal of alkylchloride, followed by distillation to remove alkyl ester. The hydroxymethyltrialkoxysilanes and carboxylic acid esters thereof, as well as carboxymethyltrialkoxysilanes, are particularly useful in sol-gel processing by undergoing hydrolysis to yield hydroxymethylsilanetriol, and subsequent hydrolysis and polycondensation products.

10 Claims, No Drawings

HYDROXYMETHYLTRIALKOXYSILANES AND METHODS OF MAKING AND USING THE SAME

STATEMENT OF GOVERNMENT INTEREST

The present invention was made in part under a grant from the Defense Advanced Research Projects Agency (DARPA), contract No. DAAH01-92C-RO38.

FIELD OF THE INVENTION

The invention is directed to novel trialkoxysilanes, precursors thereof, and condensation and hydrolysis products derived therefrom, as well as methods of making these silanes. In addition, the invention is directed to methods of using the novel trialkoxysilanes, particularly in sol-gel technology.

BACKGROUND OF THE INVENTION

Silicates are the predominant material of the earth's crust. In neutral water the silicates are soluble to the extent of 70–120 ppm and are in equilibrium with silicic acid $Si(OH)_4$, a monomeric form of silica. Silicic acid is involved in both mineralization and biomineralization of complex structures. The fabrication of silicate structures is important in both ceramic and glass technology, but traditional fabrication technologies involve the use of high temperatures.

More recently, an alternative technology, referred to as sol-gel processing, has been developed which involves the formation and condensation of silicic acid under low temperature, aqueous conditions, which may be likened to mineralization and biomineralization. Sol-gel is a method for preparing specialty metal oxide glasses and ceramics by hydrolyzing a chemical precursor or mixture of chemical precursors that pass sequentially through a solution state and a gel state before being dehydrated to a glass or ceramic. Currently, sol-gel technology entails the deposition of silicon dioxide (or other metallic or non-metallic oxides) from supersaturated solutions, usually formed by hydrolysis of reactive precursors (alkoxysilanes or other metallic or non-metallic alkoxides).

Sol-gel technology has expanded dramatically since 1980 with the development of a variety of techniques to prepare fibers, microspheres, thin films, find powders and monoliths. Applications for sol-gel technology include protective coatings, catalysts, piezoelectric devices, wave-guides, lenses, high strength ceramics, superconductors, insulating materials and nuclear waste encapsulation. The flexibility of sol-gel technology allows unique access to multicomponent oxide systems and low temperature process regimens.

Preparation of metal oxides by the sol-gel route proceeds through three basic steps: 1) partial hydrolysis of metal alkoxides to form reactive monomers; 2) the polycondensation of these monomers to form colloid-like oligomers (sol formation); 3) additional hydrolysis to promote polymerization and cross-linking leading to a 3-dimensional matrix (gel formation). Although presented sequentially, these reactions occur simultaneously after the initial processing stage.

Monomer formation (partial hydrolysis)

-continued

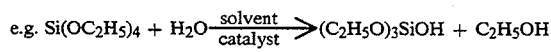

Sol formation (polycondensation)

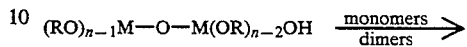

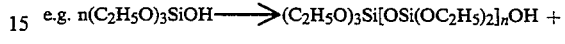

Gelation (cross-linking)

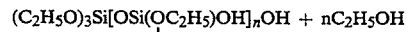

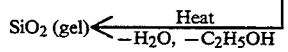

As polymerization and cross-linking progress, the viscosity of the sol gradually increases until the sol-gel transition point is reached. At this point the viscosity abruptly increases and gelation occurs. Further increases in cross-linking are promoted by drying and other dehydration methods. Maximum density is achieved in a process called densification in which the isolated gel is heated above its glass transition temperature. The densification rate and transition (sintering) temperature are influenced primarily by the morphology and composition of the gel.

The sol-gel process allows the preparation of gels (amorphous or nearly amorphous, optically-clear, homogeneous solid) under various physical forms, including (1) fine, uniform and very reactive powders from rapid hydrolysis and drying at low temperature (less than 90° C.); (2) optically clear, monolithic pieces from a slow hydrolyis route in a shaped container; or (3) films or fibers directly prepared from the viscous state of the alkoxide solution, or grown inside the solution. For a good description of sol-gel processing, see Ph. Colomban, "Gel Technology in Ceramics, Glass-Ceramics and Ceramic-Ceramic Composites," *Ceramics International* 15:23–50 (1989).

The synthesis of light-weight silicate-based ceramic structures by sol-gel techniques is of enormous current interest. However, these sol-gel systems are unstable, difficult to control, and usually contain by-products which must be removed from the matrix. In order for sol-gel processing to achieve its full potential in the production of silicates, stress-free, low-shrinkage gels must be produced from highly concentrated silicate solutions containing minimum amounts of by-products. Therefore, it would be advantageous to be able to prepare an analog of silicic acid which has greater stability in aqueous solutions than silicic acid and allows greater synthetic control in the preparation of silicate structures.

BRIEF SUMMARY OF THE INVENTION

According to the present invention, a novel class of trialkoxysilanes has been produced, namely hydroxymethyltrialkoxysilanes, which are precursors by hydrolysis to a simple analog of silicic acid, namely hydroxymethylsilanetriol and its condensation products, $HOCH_2SiO_{1.5}+-CH_2SiO_2$. Preferred hydroxymethyltrialkoxysilanes include hydroxymethyltrimethoxysilane and hydroxymethyltriethoxysilane. Both hydroxymethyltrialkoxysilanes and hydroxymethylsilanetriol undergo autocondensation reactions, forming organosilicate structures, such as films and gels, which may be converted by sintering at relatively low temperatures to produce silicon dioxide.

According to other aspects of the invention, methods are disclosed for producing hydroxymethyltrialkoxysilanes by transesterifying carboxylic acid esters of hydroxymethyltrialkoxysilanes, preferably acetoxymethyltrialkoxysilane, with an alcohol and distilling the reaction mixture to remove the carboxylic acid ester of the alcohol. The carboxylic acid esters of hydroxymethyltrialkoxysilanes may themselves be hydrolyzed to hydroxymethylsilanetriol and its condensation products. The carboxylic acid esters of hydroxymethyltrialkoxysilanes may be prepared by reaction of an alkali metal carboxylate with chloromethyltrialkoxysilane, which in turn may be prepared by the reaction of an alcohol or trialkylorthoester (e.g., formate) with chloromethyltrichlorosilane. Alternatively, the hydroxymethyltrialkoxysilanes may be made by reaction of an alcohol with carboxymethyltrialkoxysilane, also named (trialkoxysilylmethyl)formate, a novel precursor.

DETAILED DESCRIPTION OF PREFERRED EMBODIMENT

Hydroxymethylsilanetriol appears to be a synthetic analog of silicic acid which can form new structures analogous to silicates and has greater stability in aqueous solutions. It has been discovered that certain organoalkoxysilanes, namely hydroxymethyltrialkoxysilanes, are precursors to hydroxymethylsilanetriol, $HOCH_2Si(OH)_3$, and its condensation products, particularly $HOCH_2SiO_{1.5}$ and $-CH_2-SiO_2$.

The hydroxymethyltrialkoxysilanes of the invention have the formula:

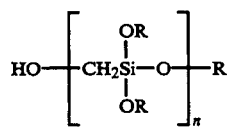

(I)

Where R is an alkyl group and n is at least 1. The alkyl group is preferably a lower alkyl group having 1 to 6 carbon atoms, and preferably 1 to 3 carbon atoms. Particularly preferred are the silanes in which the alkyl group is methyl or ethyl, namely hydroxymethyltrimethoxysilane and hydroxymethyltriethoxysilane when n in formula I is equal to 1.

The invention will now be described with particular reference to the preparation and use of hydroxymethyltriethoxysilane, but it will be understood that the following procedures are equally applicable with minor adjustments to the preparation and use of hydroxymethyltrimethoxysilane and other hydroxymethyltrialkoxysilanes.

Hydroxymethyltriethoxysilanes may be prepared according to the following scheme:

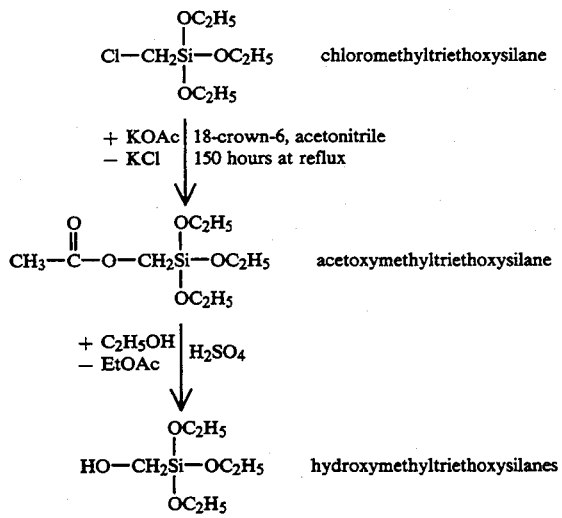

Hydroxymethyltriethoxysilane is not stable in pure form, but equilibrates in ethanol solution to various oligomers and polymers. At low concentrations of hydroxymethyltriethoxysilane in ethanol the oligomers are of low enough molecular weight to be observed by GLC. At high concentrations of hydroxymethyltriethoxysilane the formation of polymers can be observed by $Si^{29}$ FTNMR. Ultimately, if ethanol is removed from the equilibrium mixture, a clear rubbery insoluble polymer, poly(diethoxysilmethyleneoxide) is formed. On extended exposure to ethanol the insoluble polymer equilibrates to hydroxymethyltriethoxysilane. The degree of polymerization is proportional to the mole ratio of hydroxymethyltriethoxysilane to ethanol. Most of the gel examples were performed with a solution containing 50% ethanol, monomer and ~6% oligomers.

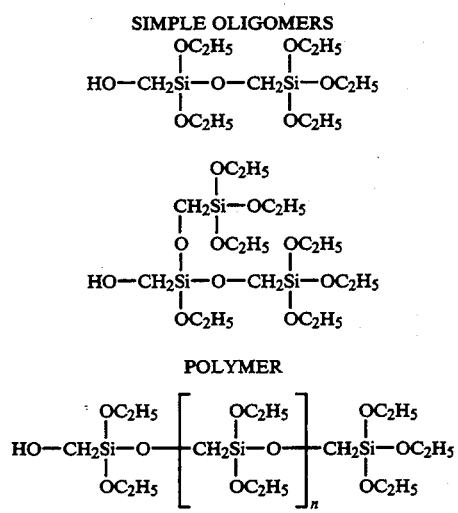

The invention will now be illustrated in more detail with reference to the following specific, nonlimiting preparation examples. In all examples temperatures are given in ° C. and pressures in mm Hg unless otherwise stated.

PREPARATION EXAMPLE 1

(a) Preparation of chloromethyltriethoxysilane $$\text{ClCH}_2\text{SiCl}_3 + 3(\text{EtO})_3\text{CH} \longrightarrow \text{ClCH}_2\text{Si}(\text{OEt})_3 + 3\text{EtCl} + 3\text{EtOOCH}$$

|      | ClCH$_2$SiCl$_3$ | 3(EtO)$_3$CH | ClCH$_2$Si(OEt)$_3$ | 3EtCl | 3EtOOCH |
|------|------|--------|-----------|-------|-------|
| M.W. | 183.92 | 148.20 | 212.75 | 64.52 | 74.08 |
| b.p. | 117–8° | 146° | 90–1°/25 mm | 12° | 52–4° |
| d    | 1.465 | 0.891 | 1.048 | 0.891 | 0.917 |

A 3-neck 1 L flask equipped with magnetic stirrer, addition funnel, pot thermometer and water-cooled condenser with nitrogen blanket was charged with 555.75 g (410 ml or 3.75 mole, i.e. a 25% excess) of triethylorthoformate and warmed to 35°–40°. 183.9 g (125.5 ml or 1M) of chloromethyltrichlorosilane was added dropwise. At about ⅓ addition, evolution of ethylchloride became evident. After the addition was complete the mixture was heated to reflux until ethylchloride evolution slowed. The mixture was stripped to a pot temperature of 160° and then allowed to cool and switched to vacuum. The product fraction, identified by IR as chloromethyltriethoxysilane, was collected at 82°–5°/15 mm. Purity: 98.3%; Yield: 92%.

Physical Properties—Chloromethyltriethoxysilane
 boiling point: 92°–5° at 15 mm; (extrapolated atmospheric b.p.: 195°–200°)
 density: 1.048 at 20° lit
 IR—strong: 2980, 1085, 801

(b) Preparation of acetoxymethyltriethoxysilane $$\text{ClCH}_2\text{Si}(\text{OEt})_3 + \text{K}^{+-}\text{OOCCH}_3 \xrightarrow{\text{CH}_3\text{CN, 18-6}} \text{CH}_3\text{COOCH}_2\text{Si}(\text{OEt})_3 + \text{KCl}$$

|      | ClCH$_2$Si(OEt)$_3$ | K$^{+-}$OOCCH$_3$ |  | CH$_3$COOCH$_2$Si(OEt)$_3$ | KCl |
|------|------|-------|------|-------|-------|
| M.W. | 212.75 | 98.15 | 41.05 | 236.34 | 74.56 |
| b.p. | 90–1°/25 |  | 82° | 106°/25 mm - observed |  |
| d    | 1.048 |  |  | 1.042 @ 25° - observed |  |

A 2 L 3-neck flask equipped with mechanical stirrer, pot thermometer and reflux condenser blanketed with nitrogen was charged with 1 liter of acetonitrile, 1 gram of 18-crown-6, 196 g (2 mole or a 100% excess) of potassium acetate and 212.75 g (1 mole) of chloromethyltriethoxysilane from (a) above. With agitation the mixture was brought to reflux for four hours and then temperature reduced to just below reflux (pot temperature 80°–84°). Reaction progress was monitored by GC. A full week of stirring was required to achieve ~90% conversion. The reaction mixture was allowed to cool. The supernatant was decanted from the salts through a Buechner funnel. The salts were washed with an additional 400 mls of acetonitrile and filtered on a Buechner. The combined supernatants were stripped at atmospheric pressure. Pot temperature was allowed to reach 120°. The formation of new high boiling products observed by GC suggested that atmospheric distillation of the product should not be attempted. The mixture was distilled at 15 mm Hg through a heated glass helix packed column. Overall recovered yield was 81%. A fraction of 104 g assayed at 99+% by GC and was employed for physical property and spectroscopic evaluation.

Physical Properties—Acetoxymethyltriethoxysilane
 boiling point: 106° at 15 mm; (extrapolated atmospheric b.p.: 225°–230°)
 density: 1.0042 at 25°
 IR—strong: 2977, 1746, 1080
 NMR—C$^{13}$: 58.98, 51.49, 28.28, 19.36 —Si$^{29}$: −54.2

(c) Preparation of hydroxymethyltriethoxysilane $$\text{CH}_3\text{COOCH}_2\text{Si}(\text{OEt})_3 + \text{C}_2\text{H}_5\text{OH} \xrightarrow{\text{H}_2\text{SO}_4} \text{HOCH}_2\text{Si}(\text{OEt})_3 + \text{C}_2\text{H}_5\text{OOCCH}_3$$

|      | CH$_3$COOCH$_2$Si(OEt)$_3$ | C$_2$H$_5$OH |  | HOCH$_2$Si(OEt)$_3$ | C$_2$H$_5$OOCCH$_3$ |
|------|-------|-------|-------|--------|-------|
| M.W. | 236.34 | 46.07 | 98.08 | 194.31 | 88.11 |
| b.p. | 106°/15 | 78° |  |  | 76–7° |
| d    | 1.01 | 0.785 | 1.94 |  | 0.902 |

A 250 ml single neck round bottom flask was charged with 42 g (0.178 mole) of acetoxymethyltriethoxysilane from (b) above, and 100 mls (78.5 g, ~10 mole excess) of 2B denatured ethanol containing 0.16 g of sulfuric acid. The flask was equipped with a short unpacked column and distillation head protected with a nitrogen blanket. The mixture was stirred at reflux for 24 hours. Approximately 50 mls of distillate was removed. The distillate had the characteristic odor, confirmed by IR, of ethylacetate. An additional 50 mls of ethanol was added to the flask and the process repeated twice. The mixture was stripped to a pot temperature of ~100° at 1 mm. A clear polymer of hydroxymethyltriethoxysilane, identified as poly(diethoxysilmethylene oxide) formed. The polymer had weak IR adsorption at 1745 indicating the presence of 2–6% acetoxymethyl groups.

The above experiment was repeated except that instead of stripping the reaction mixture in vacuum 0.15 g of sodium bicarbonate was added and 75 ml of distillate was removed from the mixture. 75 ml of additional alcohol was added. The mixture was filtered. Distillation was resumed. Sufficient material was removed to reduce the mass of the reaction to 70 g (50%). GC of the solution showed a large component with an extrapolated boiling point of 210°–220°, but higher peaks were significant.

Physical Properties—Hydroxymethyltriethoxysilane
 boiling point: unstable; (extrapolated atmospheric b.p.: 210°–220°)
 IR—strong: 3390, 2976, 2885, 1188, 1079, 982
 NMR—Si$^{29}$: −52.9

PREPARATION EXAMPLE 2

(a) Preparation of chloromethyltrimethoxysilane $$\text{ClCH}_2\text{SiCl}_3 + 3(\text{MeO})_3\text{CH} \longrightarrow \text{ClCH}_2\text{Si}(\text{OMe})_3 + 3\text{MeCl} + 3\text{MeOOCH}$$

|      | ClCH$_2$SiCl$_3$ | 3(MeO)$_3$CH | ClCH$_2$Si(OMe)$_3$ | 3MeCl | 3MeOOCH |
|------|------|--------|------|------|------|
| M.W. | 183.92 | 106.12 | 170.65 | 50.49 | 60.05 |
| b.p. | 117–8° | 101–2° | 157° | −24° | 34° |
| d    | 1.465 | 0.970 | 1.125 | 0.92 | 0.974 |

A 3-neck 1 L flask equipped with magnetic stirrer, addition funnel, pot thermometer and water-cooled condenser with nitrogen blanket was charged with 398 g (410 ml or 3.75 mole, i.e. a threefold excess) of trimethylorthoformate (TMOF) and warmed to 35°-40°. 73.5 g (50.2 ml or 0.4 mole) chloromethyltrichlorosilane was added dropwise. At about ¼ addition, evolution of methylchloride became evident. After the addition was complete the mixture was heated to reflux until methylchloride evolution slowed. The condenser was replaced with a short (150 mm) Vigreux column and distillation head. Distillation gave the following main cuts.

| cut | weight | TMOF | ClCH₂Si(OMe)₃ |
| --- | --- | --- | --- |
| 105–125° | 84.9 g | 92% | 6% |
| 125–157° | 17.0 g | 31% | 62% |
| 157–158° | 43.5 g | 0.5% | 98.1% |

Physical Properties—Chloromethyltrimethoxysilane
  boiling point: 157°
  density: 1.125 at 20°

IR—strong: 2949, 2847, 1196, 1092, 834
(b) Preparation of acetoxymethyltrimethoxysilane

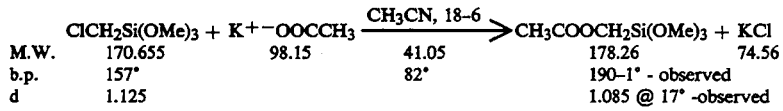

A single neck round bottom flask equipped with heating mantle, magnetic stirrer and a nitrogen protected reflux condenser was charged sequentially with 250 ml acetonitrile, 42.7 g (0.25 mole) chloromethyltrimethoxysilane from (a) above, 0.25 g 18-crown-6 and 49.1 g (0.5 mole or a 100% excess) potassium acetate. The mixture was heated to reflux. After 4 days GC indicated >90% conversion. The volume of salts in the flask was also reduced. The mixture was allowed to cool and filtered on a Buechner funnel and then distilled through a 25 cm 14/20 glass helix packed column. The best distillation cut boiled at 188°-191° at 91.5% purity. Redistillation at 190°-1° gave 95.5% purity and yielded 22 g. There appeared to be some product degradation during the distillation.
Physical Properties—Acetoxymethyltrimethoxysilane
  boiling point: 190°-1°
  density: 1.08
  IR—strong: 2949, 1740, 1235, 1100
(c) Preparation of hydroxymethyltrimethoxysilane

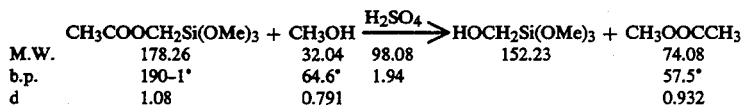

A 100 ml single neck round bottom flask was charged with 17.8 g (0.1 mole) of acetoxymethyltrimethoxysilane from (b) above, and 30 mls of methanol (23.7 g or a 600% excess) containing ~0.1 g of sulfuric acid. The flask was equipped with a short glass helix packed column and distillation head protected with a nitrogen blanket. The mixture was stirred at reflux for 4 hours. Approximately 12 mls of distillate was removed. The distillate had the characteristic odor, confirmed by IR, of methylacetate. An additional 12 mls of methanol was added to the flask and the process repeated. 0.1 g of potassium bicarbonate was added and 30 ml of distillate was removed from the mixture. The mixture was filtered. The clear product weighed 12.65 g, suggesting substantial condensation to polymer. Thin films of the product hydrolyzed on standing in air to form clear, hard films.
Physical properties—hydroxymethyltrimethoxysilane/poly(dimethoxysilmethylene oxide) mixture
  boiling point: unstable;
  IR—strong: 3424, 2949, 2845, 1193, 1077, 837

PREPARATION EXAMPLE 3

(a) Preparation of carboxymethyltriethoxysilane, also known as (triethoxysilylmethyl) formate

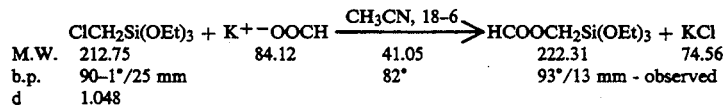

A single neck 100 ml flask equipped with magnetic stirrer and reflux condenser blanketed with nitrogen, was charged with 45 ml acetonitrile, 0.25 g 18-crown-6, 12.6 g (0.15 mole, a 50% excess) potassium formate and 21.27 g (0.1 mole) chloromethyltriethoxysilane. The mixture was heated to reflux. Reaction progress was monitored by G.C. After 24 hours ~50% conversion was observed. Reaction progressed to ~75% after 48 hours, and to ~80% after 72 hours. The mixture began to show build-up of high boilers. The mixture was filtered through glass wool to remove salts. The mixture was fractionated at reduced pressure. In the first stage acetonitrile was removed at ~100 mm. Vacuum was reduced. The product fraction boiled at 93°/13 mm-98°/17 mm. Yield was 8.8 g (40%).

In order to evaluate aqueous stability a solution of 0.5 g carboxymethyltriethoxysilane, 0.5 g of ethanol and 4.0 g of distilled water was prepared. The solution was stable for greater than 1 month.
Physical Properties—Carboxymethyltriethoxysilane
  boiling point: 93° at 13 mm; (extrapolated atmospheric b.p.: 210°-215°)
  IR—strong: 2977, 2930, 1735, 1444, 1393, 1290, 1100
(b) Preparation of hydroxymethyltriethoxysilane $$\text{HCOOCH}_2\text{Si(OEt)}_3 + \text{C}_2\text{H}_5\text{OH} \xrightarrow{\text{H}_2\text{SO}_4} \text{HOCH}_2\text{Si(OEt)}_3 + \text{C}_2\text{H}_5\text{OOCH}$$

|        | HCOOCH₂Si(OEt)₃ | C₂H₅OH | H₂SO₄ | HOCH₂Si(OEt)₃ | C₂H₅OOCH |
|--------|-----------------|--------|-------|---------------|----------|
| M.W.   | 222.31          | 46.07  | 98.08 | 194.31        | 74.01    |
| b.p.   | 93°/13 mm       | 78°    |       |               | 52–4°    |
| d      |                 | 0.785  | 1.94  |               | 0.917    |

A 50 ml single neck round bottom flask was charged with 4.4 g (0.02 mole) of carboxymethyltriethoxysilane from (a) above and 10 g (0.22 mole, ~10 fold excess) of 2B denatured ethanol containing 0.02 g of sulfuric acid. The flask was equipped with a 150 mm packed column and distillation head protected with a nitrogen blanket. The mixture was stirred at 50-60° for 25 hours. Approximately 5 g of ethyl formate/ethanol was removed by distillation. An additional 5 g of ethanol was added to the flask. After stirring the mixture at 50°-60° for 2 hours, 0.05 g of sodium bicarbonate was added. The mixture was stirred 1 hour additional without heating, and then the solution was decanted through glass wool to remove sodium bicarbonate/sodium sulfate. The mixture was returned to the flask and distillation was resumed. Sufficient material was removed to reduce the mass of the reaction to 7.8 g (~50% product concentration). As in the case of product prepared by transesterifaction of the acetate, GC of the solution showed a large component with an extrapolated boiling point of 210°-220° but higher peaks were significant. IR, NMR results were as reported in Preparation Example 1(c).

Hydroxymethyltrialkoxysilanes and low-molecular weight alcohol soluble oligomers are readily hydrolyzed to hydroxymethylsilanetriol which immediately begins undergoing autocondensation. Visually, upon mixing with water, turbidity develops and then clears in minutes to hours depending on the concentration of the silane, alcohol and pH of the water. This is consistent with the general course of hydrolysis of monoorganotrialkoxysilanes previously described in which the initially immiscible silane hydrolyzes to form soluble silanol containing species.

In contrast to most monoorganotrialkoxysilanes and the silicic acid precursor, tetraethoxysilane, the hydrolysis products of hydroxymethyltriethoxysilane have significantly greater solubility and stability in aqueous solutions. The solutions are stable for at least six months at concentrations up to 15% in 1:1.5 ethanol-water mixtures. Silicic acid is stable in neutral aqueous solutions only at concentrations below 100 ppm. The increased solubility is presumably due to the polarity and hydrogen-bonding of the hydroxymethyl group, allowing oligomeric species to remain soluble past the limit of trimer typically observed for monoalkyltrialkoxysilanes.

The increased stability is at least partly due to the reversible condensation of the hydroxymethyl group with silanol. The equilibrium constant for esterification of silanols has been shown to be ~2.5×10⁻² suggesting that the presence of the hydroxymethyl group, hydrolysis and solution ethanol tie up a sufficient portion of the pool of soluble silicate species to inhibit formation of high molecular weight, insoluble siloxanes.

The course of hydrolysis may be followed in more detail by Si²⁹ NMR. Upon mixing with water the resonance at −52.9 ppm associated with hydroxymethyltriethoxysilane disappears and is replaced with a multiplicity of resonances which, in addition to the simple monomer hydroxymethylsilanetriol, may be associated with three main classes of compounds, i.e., siloxane bridged, silmethyleneoxide bridged, and mixed condensates:

HYDROXYMETHYLSILANETRIOL

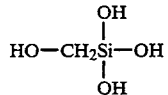

SILMETHYLENEOXIDE BRIDGED

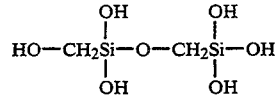

SILOXANE BRIDGED

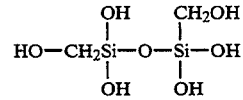

The analogous hydrolysis products of the carboxylic acid esters of hydroxymethyltrialkoxysilanes are ultimately similar to those discussed above but pass through the intermediate stage of carboxylic acid esters of hydroxymethylsilanetriols. For example, acetoxymethyltrialkoxysilanes hydrolyze first to acetoxymethylsilanetriols, which may then be further hydrolyzed and polycondensed as described herein for hydroxymethyltrialkoxysilanes.

The compounds of the invention appear to have particularly utility in the area of sol-gel derived ceramics, in which metal alkoxides are hydrolyzed under controlled conditions, to form coatings, films, monoliths and powders, as generally described above in the background section. Accordingly, the use of the compounds of the invention will now be illustrated in more detail with reference to the following specific, non-limiting examples.

Gel Examples

Gels were formed from acetoxymethyltriethoxysilane and hydroxymethyltriethoxysilane in a two-step hydrolysis method analogous to that described below for tetraethoxysilane. Initially a mixture of silane:water:ethanol:HCl was prepared at a ratio of 1.5:5:10⁻³ and stirred for 30 minutes. An additional 1.5 to 3.2 equivalents of water was added. The solutions were poured into round dishes and stored quiescently. Clear gels formed in 12-24 hours. After hours they were dried at 110° C.

| compound         | M.W.   | g     | ml              | mole % |
|------------------|--------|-------|-----------------|--------|
| tetraethoxysilane| 208.33 | 22.7  | 24.3            | 10.9   |
| ethanol          | 46.07  | 27.36 | 34.6            | 54.9   |
| water            | 18.02  | 3.78  | 3.78            | 21.0   |
| HCl              | 36.5   | .365  | 0.1 ml of 1M sol'n |     |

The compounds were mixed (HCl last) and stirred 20 minutes. Water was added in the aliquots listed and ml of solution removed and cast for gel formation.

| Sample | Water Aliquot | 14 hr | 24 hr | 38 hr | 110° at 48 hr |
|---|---|---|---|---|---|
| 1 | 6 ml | gel/cracks | shatter | shatter/warp | micro-cracks |
| 2 | 6 ml | gel | cracks | large pieces | micro-cracks |
| 3 | 6 ml | gel/cracks | cracks | large pieces | cracks |
| 4 | 3 ml | liquid | gel | shatter | cracks |

(2) Acetoxymethyltriethoxysilane (monoorganoalkoxysilane control)

| compound | M.W. | g | ml | mole % |
|---|---|---|---|---|
| acetoxymethyl-triethoxysilane 50% in ethanol | 236.34 | 19.5 | | 10.6 |
| ethanol | 46.07 | 2.8 | (12.5 w/adj) | 69.9 |
| water | 18.02 | 1.35 | | 19.4 |
| HCl | 36.5 | .146 | 0.04 ml of 1M sol'n | |

The compounds were mixed (HCl last) and stirred 20 minutes. Water was added in the aliquots listed and 6.75 ml of solution removed and cast for gel formation.

| Sample | Water Aliquot | 14 hr | 24 hr | 38 hr | 110° at 48 hr |
|---|---|---|---|---|---|
| 1 | 2.75 ml | gel/curl | few cracks | large pieces | micro-cracks |
| 2 | 2.75 ml | liquid | gel-opalescent | large pieces | micro-cracks |
| 3 | 2.75 ml | liquid/opaque | liquid opaque | slight gel/dry out | no cracks |
| 4 | 1.4 ml | liquid | liquid | dry-opaque | white solid |
| 5 | 1.4 ml | liquid | liquid | dry-opaque | white solid |

The dried gels formed from acetoxymethyltriethoxysilane were indefinitely stable to water, but in contrast to gels formed from tetraethoxysilane, dissolved in cold sulfuric acid overnight. Thermogravimetric analysis of dried gels in air at 10°/min showed gradual loss of approximately 5% of weight up to 200°, presumably associated with further condensation and loss of water. At higher temperatures the rate of weight loss increased to a maximum at 430°, finally stabilizing at 670° at 60% of initial dry weight.

(3) Hydroxymethyltriethoxysilane

| compound | M.W. | g | ml | mole % |
|---|---|---|---|---|
| hydroxymethyl-triethoxysilane 50% in ethanol | 195.31 | 19.5 | | 12.6 |
| ethanol | 46.07 | 2.8 | (12.5 w/adj) | 68.4 |
| water | 18.02 | 1.35 | | 19.0 |
| HCl | 36.5 | .146 | 0.04 ml of 1M sol'n | |

The compounds were mixed (HCl last) and stirred 20 minutes. Water was added in the aliquots listed and 7.5 ml of solution removed and cast for gel formation.

| Sample | Water Aliquot | 14 hr | 24 hr | 38 hr | 110° at 48 hr |
|---|---|---|---|---|---|
| 1 | 2.75 ml | gel/opalescent (no cracks) | clear/cracks | clear/large pieces | powder |
| 2 | 2.75 ml | gel/clear (no cracks) | clear/cracks | clear/large pieces | powder |
| 3 | 2.75 ml | liquid | gel/clear cracks | gel/clear cracks | clear/cracks |
| 4 | 2.75 ml | liquid | gel/clear cracks | gel/clear cracks | clear/cracks |
| 5 | 1.4 ml | liquid | gel/clear cracks | gel/clear cracks | clear/cracks |

Clear gels formed from hydroxymethyltriethoxysilane over the entire range of conditions tested in contrast to acetoxymethyltriethoxysilane. It was possible to generate thinner films with fewer fractures with hydroxymethyltriethoxysilane than with tetraethoxysilane. The dried gels formed from hydroxymethyltriethoxysilane were indefinitely stable to water and were not dissolved by cold sulfuric acid. Thermogravimetric analysis of dried gels in air at 10°/min showed gradual loss of approximately 5% of weight up to 250°, presumably associated with further condensation and loss of water. At higher temperatures the rate of weight loss increased to a maximum at 415° C. Weight loss stabilized at 670° at approximately 80% of initial dry weight. The sintered product was aa amber glass. Analysis indicated >99% $SiO_2$.

The novel compounds of the invention are expected to have utility beyond sol-gel chemistry in their monomeric and oligomeric forms by stabilizing aqueous solutions of silicates which are utilized in such applications as corrosion inhibitors for automotive anti-freeze. They are also expected to stabilize aqueous solutions of organosilanes used as water-repellents, as coupling agents, and in sealants and composites. The compounds of the invention may possibly be used as a substrate for silicate biomineralization and also as an inhibitor for the growth of certain species of diatoms.

The present invention may be embodied in other specific forms without departing from the spirit or essential attributes thereof and, accordingly, reference should be made to the appended claims, rather than to the foregoing specification as indicating the scope of the invention.

I claim:

1. A hydroxymethyltrialkoxysilane of the formula:

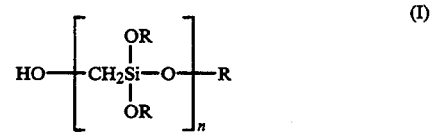

where R is an alkyl group and n is at least one.

2. A hydroxymethyltrialkoxysilane according to claim 1 where R is a $C_1$ to $C_3$ alkyl group and n=1 to 100.

3. A hydroxymethyltrialkoxysilane according to claim 1 where R is a methyl group.

4. A hydroxymethyltrialkoxysilane according to claim 1 where R is an ethyl group.

5. A hydrolysis reaction product of a hydroxymethyltrialkoxysilane wherein said product comprises hydroxymethylsilanetriol.

6. A method of producing a hydroxymethyltrialkoxysilane comprising transesterifying a carboxylic acid ester of hydroxymethyltrialkoxysilane with an alcohol, and distilling the reaction mixture to remove the carboxylate of the alcohol.

7. A method according to claim 6 wherein said transesterification is carried out in the presence of sulfuric acid, and said alcohol has the same alkyl radical as the alkoxy group of said carboxylic acid ester of hydroxymethyltrialkoxysilane.

8. A method according to claim 6 wherein said carboxylic acid ester of hydroxymethyltrialkoxysilane is prepared by reaction of an alkali metal carboxylate with chloromethyltrialkoxysilane.

9. A method according to claim 8 wherein said carboxylate reaction is carried out in the presence of an acetonitrile solvent and 18-crown-6 catalyst.

10. A method according to claim 8 wherein said chloromethyltrialkoxysilane is prepared by reaction of an alcohol or trialkylorthoester with chloromethyltrichlorosilane by heating to reflux with removal of alkyl chloride, followed by distillation to remove alkylester.

* * * * *